United States Patent
Kelly et al.

(10) Patent No.: US 7,707,130 B2
(45) Date of Patent: Apr. 27, 2010

(54) REAL-TIME PREDICTIVE COMPUTER PROGRAM, MODEL, AND METHOD

(75) Inventors: Bruce Kelly, Prairie Village, KS (US); Eugene Russell McDannald, Jr., Hawkinsville, GA (US)

(73) Assignee: Health Care Information Services LLC, Prairie Village, KS (US)

( * ) Notice: Subject to any disclaimer, the term of this patent is extended or adjusted under 35 U.S.C. 154(b) by 451 days.

(21) Appl. No.: 11/678,884

(22) Filed: Feb. 26, 2007

(65) Prior Publication Data

US 2008/0097943 A1    Apr. 24, 2008

Related U.S. Application Data

(60) Provisional application No. 60/862,528, filed on Oct. 23, 2006.

(51) Int. Cl.
    *G06F 15/18*    (2006.01)
(52) U.S. Cl. .................................................. 706/21
(58) Field of Classification Search .................. 706/21
    See application file for complete search history.

(56) References Cited

U.S. PATENT DOCUMENTS

| | | | |
|---|---|---|---|
| 6,761,697 B2 * | 7/2004 | Rubinstenn et al. | 600/587 |
| 6,859,529 B2 * | 2/2005 | Duncan et al. | 379/266.1 |
| 6,956,941 B1 * | 10/2005 | Duncan et al. | 379/265.01 |
| 7,023,979 B1 * | 4/2006 | Wu et al. | 379/265.11 |
| 7,143,091 B2 * | 11/2006 | Charnock et al. | 707/5 |
| 7,197,474 B1 * | 3/2007 | Kitts | 705/10 |
| 7,285,090 B2 * | 10/2007 | Stivoric et al. | 600/300 |
| 7,324,668 B2 * | 1/2008 | Rubinstenn et al. | 382/118 |
| 7,366,707 B2 * | 4/2008 | de Lacharriere et al. | 706/62 |
| 7,395,217 B1 | 7/2008 | Stevens et al. | |
| 7,437,344 B2 * | 10/2008 | Peyrelevade | 706/62 |
| 7,519,564 B2 * | 4/2009 | Horvitz | 706/12 |
| 7,609,150 B2 * | 10/2009 | Wheatley et al. | 340/436 |
| 7,634,103 B2 * | 12/2009 | Rubinstenn et al. | 382/100 |
| 2003/0009290 A1 | 1/2003 | Billet et al. | |
| 2006/0241972 A1 * | 10/2006 | Lang et al. | 705/2 |
| 2006/0259333 A1 | 11/2006 | Pyburn et al. | |
| 2007/0038479 A1 | 2/2007 | Kay | |
| 2007/0038480 A1 | 2/2007 | Kay | |
| 2008/0306893 A1 * | 12/2008 | Saidi et al. | 706/21 |

OTHER PUBLICATIONS

A network measurement architecture for adaptive applications Stemm, M.; Katz, R.; Seshan, S.; Infocom 2000. Nineteenth Annual Joint Conference of the IEEE Computer and Communications Societies. Proceedings. IEEE vol. 1, Mar. 26-30, 2000 pp. 285-294 vol. 1 Digital Object Identifier 10.1109/INFCOM.2000.832198.*

(Continued)

*Primary Examiner*—Michael B Holmes
(74) *Attorney, Agent, or Firm*—Hovey Williams LLP

(57) ABSTRACT

A method for predicting a future occurrence of an event involves obtaining a history of prior occurrences of the event. A plurality of variables is created that are associated with the event. Weights are assigned to each variable. An artificial neural network is accessed and trained with the history of past occurrences of the event by comparing an output of the artificial neural network to the past occurrence of the event. The weights are adjusted until the output corresponds to the past occurrence of the event.

11 Claims, 2 Drawing Sheets

OTHER PUBLICATIONS

Figure 1:
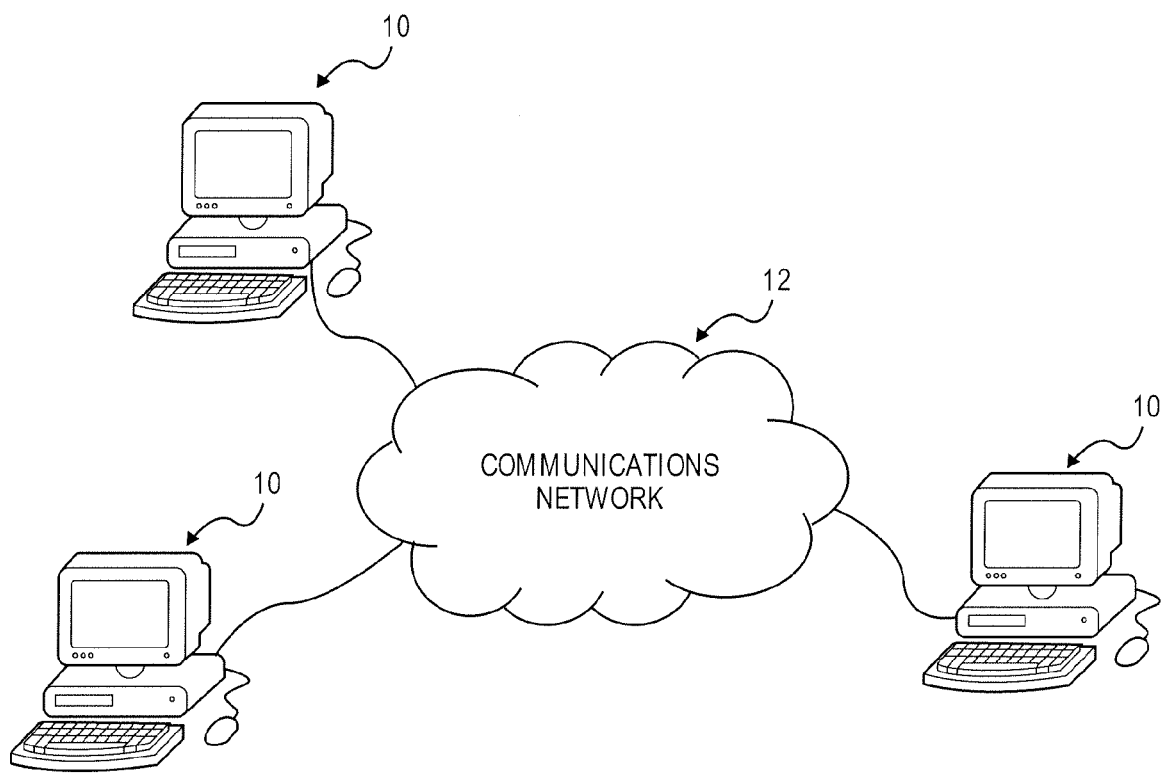

Integration of empirical RF data with propagation prediction models Lemon, D.G.; Clampitt, H.G.; Marth, C.R.; Vehicular Technology Conference, 1991. Gateway to the Future Technology in Motion., 41st IEEE May 19-22, 1991 pp. 307-313 Digital Object Identifier 10.1109/VETEC.1991.140500.*

Zurada et al., "A neural network-based system for classification of industrial jobs . . . ", Elsevier, 1997, pp. 49-58.

Chen et al., "A new approach to applying feedforward neural networks to the prediction of musculoskeletal disorder risk", Elsevier, 2000, pp. 269-282.

* cited by examiner

REAL-TIME PREDICTIVE COMPUTER PROGRAM, MODEL, AND METHOD

RELATED APPLICATION

This non-provisional application claims the benefit of U.S. Provisional Application Ser. No. 60/862,528, entitled "REAL TIME PREDICTIVE COMPUTER PROGRAM, MODEL, AND METHOD," filed Oct. 23, 2006. The identified provisional application is incorporated herein by specific reference.

BACKGROUND OF THE INVENTION

1. Field of the Invention

The present invention relates to programs, models and methods for predicting future occurrences of events. More particularly, the invention relates to a method for predicting a future occurrence of an event using a plurality of variables and an artificial neural network.

2. Description of the Related Art

Many organizations attempt to predict future events or trends to more efficiently and/or economically provide services. For example, medical facilities such as hospitals and clinics would like to determine patient-related information such as length of stay, treatment options, and pharmaceutical needs for a given ailment. Such information can help the medical facility plan for issues such as bed space, staffing concerns, and purchasing and storage of supplies. As a result, costs could be cut by not planning to provide more resources than would be necessary.

Trend forecasting and future event prediction in the past have involved accumulating data associated with the subject of the forecasting or prediction. Regression or extrapolation techniques are applied to the data to find the trend or predict future activity. However, these techniques don't take into account variable data connected with the event.

SUMMARY OF THE INVENTION

The present invention provides a distinct advance in the art of methods of predicting future occurrences of events. More particularly, the invention provides a method for predicting a future occurrence of an event that takes into account a plurality of variable data related to the event.

One embodiment of the invention is a method of predicting a future occurrence of an event. The method begins with obtaining a history of past occurrences of the event. Next, a plurality of variables that are associated with the event are created, and a weight is assigned to each variable. An artificial neural network is then created. The artificial neural network is trained with the history of occurrences of the event by applying the variables associated with the event to the artificial neural network and comparing an output of the network with a past occurrence of the event. The method is completed by adjusting the weights of the variables such that the output of the network corresponds to the past occurrence of the event.

An exemplary embodiment of the invention is a method of predicting a worker's compensation injury. The method begins with obtaining a history of worker's injuries requiring worker's compensation. Next, an artificial neural network is accessed. Then, the artificial neural network is trained with the history of worker's compensation injuries to predict the next occurrence of a worker's compensation injury.

Another exemplary embodiment of the invention is a method of predicting an acute medical situation. The method begins by obtaining a history of acute medical situations of a patient. Next, an artificial neural network is accessed. Then, the artificial neural network is trained with the history of acute medical situations to predict the occurrence of the next acute medical situation.

Other aspects and advantages of the present invention will be apparent from the following detailed description of the preferred embodiments and the accompanying drawing figures.

BRIEF DESCRIPTION OF THE DRAWING FIGURES

Figure 2:
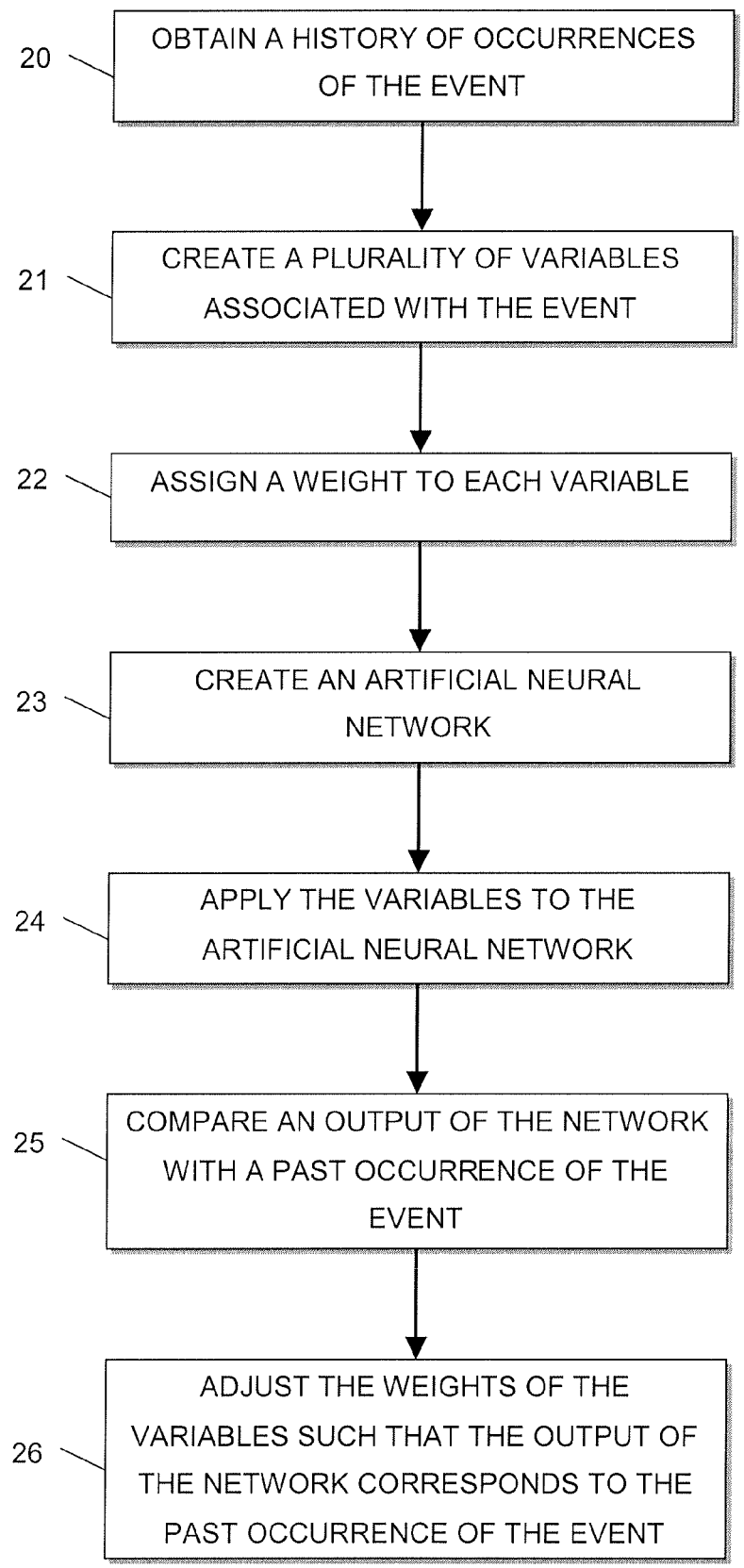

A preferred embodiment of the present invention is described in detail below with reference to the attached drawing figures, wherein:

FIG. 1 is a schematic diagram illustrating some of the elements operable to be utilized by various embodiments of the present invention; and FIG. 2 is a flow diagram showing some of the steps operable to be performed by various embodiments of the present invention.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE PREFERRED EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Methods consistent with the present teachings are especially well-suited for implementation by a computing element, such as the computer 10 illustrated in FIG. 1. The computer 10 may be a part of a computer network that includes one or more client computers and one or more server computers interconnected via a communications system 12 such as an intranet, the internet a wireless network, or any other communications network. The present invention will thus be generally described herein as a computer program. It will be appreciated, however, that the principles of the present invention are useful independently of a particular implementation, and that one or more of the steps described herein may be implemented without the assistance of the computing device.

The present invention can be implemented in hardware, software, firmware, or a combination thereof. In a preferred embodiment, however, the invention is implemented with a computer program. The computer program and equipment described herein are merely examples of a program and equipment that may be used to implement the present invention and may be replaced with other software and computer equipment without departing from the scope of the present teachings.

Computer programs consistent with the present teachings can be stored in or on a computer-readable medium residing on or accessible by a host computer for instructing the host computer to implement the method of the present invention as described herein. The computer program preferably comprises an ordered listing of executable instructions for implementing logical functions in the host computer and other computing devices coupled with the host computer. The computer program can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions.

The ordered listing of executable instructions comprising the computer program of the present invention will hereinafter be referred to simply as "the program" or "the computer program." It will be understood by persons of ordinary skill in the art that the program may comprise a single list of executable instructions or two or more separate lists, and may be stored on a single computer-readable medium or multiple distinct media. In the context of this application, a "software object" is a programming unit that groups together a data structure (e.g., instance variables) and the operations (e.g., methods) that can use or affect that data.

In the context of this application, a "computer-readable medium" can be any means that can contain, store, communicate, propagate or transport the program for use by or in connection with the instruction execution system, apparatus, or device. The computer-readable medium can be, for example, but not limited to, an electronic, magnetic, optical, electro-magnetic infrared, or semi-conductor system, apparatus, device, or propagation medium. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disc (CD) or a digital video disc (DVD). The computer-readable medium could even be paper or another suitable medium upon which the program is printed, as the program can be electronically captured, via for instance, optical scanning of the paper or other medium, then compiled, interpreted, or otherwise processed in a suitable manner, if necessary, and then stored in a computer memory.

The steps of an embodiment of the method that create a model for predicting a future occurrence of an event utilized by various embodiments of the present invention are illustrated in the flow diagram of FIG. 2. The method begins at step 20 by obtaining a history of past occurrences of the event. Thus, the event has to have already happened to predict a future occurrence. Embodiments of the present invention are not operable to be utilized in predicting the occurrence of an event that has not already occurred. Furthermore, embodiments of the present invention require a minimum of twenty-five occurrences of the event in order to properly predict a future occurrence of the event. Generally, as the number of prior occurrences of the event increases, so does the accuracy of the prediction of future occurrences of the event.

The next step 21 of the method is to create a plurality of variables associated with the event. Considerations for the creation of variables include but are not limited to: geographical location of the event, environmental conditions during the event, ages of entities involved with the event, sizes of entities involved with the event, shapes of entities involved with the event, physical condition of entities involved with the event, quantities of entities involved with the event, costs associated with the event, measurable properties of entities involved with the event, and miscellaneous factors.

Each variable created in step 21 has a weight assigned to it in step 22. The weight is a multiplication factor for the input variable data. In various embodiments of the present invention, the weight is a value that is greater than 0 and less than 1, such that the sum of all weights is equal to 1.

In step 23, an artificial neural network (ANN) is created in various embodiments. In other embodiments, an already-existing ANN is accessed. In the preferred embodiment, a feed-forward, back-propagate type of ANN is utilized. Other types of ANNs could be utilized as well, such as the delta bar delta, the extended delta bar delta, and the directed random search.

Once the ANN is created or chosen, the ANN must be trained with the history of occurrences of the event. In preferred embodiments, the training is accomplished with supervised training. The training begins as indicated in step 24 with applying the variable data to the ANN. An output of the ANN is compared a past occurrence of the event in step 25. Then in step 26, the weights of the variables are adjusted such that the output of the ANN corresponds to the past occurrence of the event. The training is repeated for each occurrence of the event.

The following examples further illustrate the method of predicting a future occurrence of an event as utilized in various embodiments of the present invention.

The method can be used, for example, to create a model to predict a future occurrence of a worker's compensation injury. In preferred embodiments, the method begins with obtaining a history of at least twenty-five prior occurrences of worker's injuries that required worker's compensation. Next, a list of variables associated with worker's compensation injuries is created. Weights are assigned to each variable. One possible set of variables associated with worker's compensation injuries is listed in Table 1. Other variables could be added as experience determines they are relevant to the prediction.

TABLE 1

Listing of variables associated with worker's compensation injuries

| Variables | Initial Weighting For ANN's | Final Weighting For ANN's |
|---|---|---|
| Pre-morbidity status | 7% | 8% |
| Post-event status | 7% | 10% |
| Post-medical condition | 7% | 8% |
| Hospitalization | 7% | 10% |
| Support at home | 7% | 9% |
| Availability of home care | 7% | 4% |
| Availability of outpatient services | 7% | 4% |
| Suitability of individual for his job | 7% | 10% |
| Availability of light-duty work | 7% | 6% |
| Availability of job retraining | 7% | 8% |
| Potential for litigation | 7% | 6% |
| State in which injury occurred | 7% | 10% |
| Miscellaneous | 16% | 7% |
| | 100% | 100% |

Table 1 also shows the initial weights for each variable. Once the variables are determined, an ANN is chosen and trained with the history of worker's compensation injuries. For each injury, the variable data is applied and an output of the ANN is compared with the occurrence of the injury. The weights are adjusted until the output of the ANN corresponds to the occurrence of each past injury. The final weights for this example are also listed in Table 1.

In addition to predicting a future occurrence of a worker's compensation injury, the model could also be used to predict, among other things, an anticipated date of hospital discharge, if the disability will be permanent, if retraining will be necessary to reenter the workplace, an anticipated time for return to work, type of work status, the need and timing for rehabilitation services, the need and timing for independent medical evaluation, and the probability of potential litigation.

Another example in which the method of various embodiments of the present invention could be utilized is predicting an acute medical situation. In preferred embodiments, the method begins with obtaining a history of at least twenty-five prior illnesses. Next, a list of variables associated with acute medical situations is created. Weights are assigned to each variable. One possible set of variables associated with acute medical situations is listed in Table 2. Other variables could be added as experience determines they are relevant to the prediction.

TABLE 2

Listing of variables associated with acute medical situations

| Variables | Initial Weighting For ANN's | Final Weighting For ANN's |
|---|---|---|
| Pre-morbidity status | 6% | 3% |
| Post-event status (day 2) | 6% | 7% |
| Post-event status (day 3) | 6% | 7% |
| Post-event status (day 4) | 6% | 7% |
| Post-event status (day 5) | 6% | 6% |
| Co-morbidities | 6% | 8% |
| Medications | 6% | 7% |
| X-rays/diagnostic tests | 6% | 5% |
| Laboratory tests | 6% | 5% |
| Physical therapy | 6% | 7% |
| Occupational therapy | 6% | 7% |
| Activities of daily living | 6% | 7% |
| Surgeries | 6% | 8% |
| Support at home | 6% | 8% |
| Availability of home care | 6% | 4% |
| Miscellaneous | 10% | 4% |
| | 100% | 100% |

The initial weighting of the variables is also listed in Table 2. Next, an ANN is chosen and trained with the history of illnesses. For each illness, the variable data is applied and an output of the ANN is compared with the occurrence of the illness. The weights are adjusted until the output of the ANN corresponds to the occurrence of each past illness. The final weights for this example are also listed in Table 2.

Using the same acute medical situation predictive model, the method of various embodiments of the present invention could also be used to predict, among other things, length of hospital stay, the length of time post-discharge services, the need for home health services, outpatient therapy services, and pharmaceutical needs. The acute medical situation model could also be used to predict events for pediatric medical care.

A similar example to the acute medical situation example is using the method of various embodiments of the present invention to predict an individual's wellness. The method requires a history of at least twenty-five past illnesses and a variable set related to an individual's wellness with initial weights. One possible set of variables associated with wellness is listed in Table 3. Other variables could be added as experience determines they are relevant to the prediction.

TABLE 3

Listing of variables associated with individual wellness

| Variables | Initial Weighting For ANN's | Final Weighting For ANN's |
|---|---|---|
| Current medical status | 6% | 7% |
| Family history | 6% | 8% |
| Co-morbidities | 6% | 7% |
| Laboratory data | 6% | 6% |
| X-ray data | 6% | 6% |
| Past medical history | 6% | 8% |
| Weight | 6% | 8% |
| Height | 6% | 5% |
| Lifestyle | 6% | 6% |
| Blood pressure | 6% | 6% |
| Cholesterol level | 6% | 7% |
| Worker's compensation injuries | 6% | 5% |
| Vaccinations | 6% | 3% |
| Stress level | 6% | 4% |
| Exercise level | 6% | 8% |
| Miscellaneous | 10% | 4% |
| | 100% | 100% |

An ANN is chosen and trained with the history of illnesses. For each illness, the variable data is applied and an output of the ANN is compared with the occurrence of the illness. The weights are adjusted until the output of the ANN corresponds to the occurrence of each past illness. The initial and final weights for this example are listed in Table 3.

In various embodiments, this model can be used to predict future medical events and illnesses for an individual, thus anticipating the need for wellness programs, wellness lifestyle changes, and medical care intervention.

Another example in which the method of various embodiments of the present invention could be utilized is predicting premature/neo-natal births. In preferred embodiments, the method begins with obtaining a history of at least twenty-five prior births. Next, a list of variables associated with pregnancy is created. Weights are assigned to each variable. One possible set of variables associated with pregnancy is listed in Table 4. Other variables could be added as experience determines they are relevant to the prediction.

TABLE 4

Listing of variables associated with premature/neo-natal births

| Variables | Initial Weighting For ANN's | Final Weighting For ANN's |
|---|---|---|
| Time of complete blood chemistry analysis | 12% | 10% |
| Time of exam by OB/GYN | 12% | 10% |
| Cross-linked collagen diagnosis | 12% | 20% |
| Prescription of proper medication | 12% | 20% |
| Commencement of wellness program | 12% | 10% |
| Cessation of smoking | 12% | 10% |
| Cessation of alcohol consumption | 12% | 9% |
| Cessation of drug use | 12% | 9% |
| Miscellaneous | 4% | 2% |
| | 100% | 100% |

An ANN is chosen and trained with the history of births. For each birth, the variable data is applied and an output of the ANN is compared with the occurrence of the birth. The weights are adjusted until the output of the ANN corresponds to the occurrence of each past birth. The initial and final weights for this example are listed in Table 4. The model of this example can be used to predict a premature/neo-natal birth, thereby allowing medical staff to take preventative action to avoid such a situation.

Another example in which the method of various embodiments of the present invention could be utilized is predicting animal illnesses in a veterinary medical practice. In preferred embodiments, the method begins with obtaining a history of at least twenty-five prior animal illnesses. Next, a list of variables associated with the veterinary practice is created. Weights are assigned to each variable. One possible set of variables associated with veterinary practices is listed in Table 5. Other variables could be added as experience determines they are relevant to the prediction.

TABLE 5

Listing of variables associated with a veterinary medical practice

| Variables | Initial Weighting For ANN's | Final Weighting For ANN's |
|---|---|---|
| Number of veterinarians | 5% | 4% |
| Number of vet assistants | 5% | 3% |
| Size of animal clinic | 5% | 2% |
| Size of client base | 5% | 5% |
| Size of household base | 5% | 5% |
| Number of large dogs (>= 30 lbs) | 5% | 6% |
| Number of small dogs (<30 lbs) | 5% | 6% |
| Number of cats | 5% | 6% |
| Number of large-dog surgeries | 5% | 7% |
| Number of small-dog surgeries | 5% | 7% |
| Number of cat surgeries | 5% | 7% |
| Number of office support staff | 5% | 2% |
| Human population of service area | 5% | 3% |
| Average charge per visit | 5% | 4% |
| Average charge per surgery | 5% | 7% |
| Average charge per household | 5% | 3% |
| Cost of supplies per visit | 5% | 4% |
| Cost of supplies per surgery | 5% | 7% |
| Number of specialty referrals per veterinarian | 5% | 8% |
| Miscellaneous | 5% | 8% |
|  | 100% | 100% |

An ANN is chosen and trained with the history of animal illnesses. For each illness, the variable data is applied and an output of the ANN is compared with the occurrence of the illness. The weights are adjusted until the output of the ANN corresponds to the occurrence of each past animal illness. The initial and final weights for this example are listed in Table 5.

Another example in which the method of various embodiments of the present invention could be utilized is predicting the occurrence of an oil or gas pipeline failure. In preferred embodiments, the method begins with obtaining a history of at least twenty-five prior pipeline failures. Next, a list of variables associated with the pipeline is created. Weights are assigned to each variable. One possible set of variables associated with pipelines is listed in Table 6. Other variables could be added as experience determines they are relevant to the prediction.

TABLE 6

Listing of variables associated with pipelines

| Variables | Initial Weighting For ANN's | Final Weighting For ANN's |
|---|---|---|
| Manufacturer of pipe | 7% | 8% |
| Type of pipe | 7% | 10% |
| Diameter of pipe | 7% | 8% |
| Location of pipe | 7% | 10% |
| Type of valve | 7% | 9% |
| Manufacturer of valve | 7% | 4% |
| Diameter of valve | 7% | 4% |
| Location of valve | 7% | 10% |
| Topography | 7% | 6% |
| Climate | 7% | 8% |
| Pressure in pipeline | 7% | 6% |
| Corrosiveness of pipeline contents | 7% | 10% |
| Age of pipeline | 7% | 16% |
| Miscellaneous | 9% | 7% |
|  | 100% | 100% |

An ANN is chosen and trained with the history of pipeline failures. For each failure, the variable data is applied and an output of the ANN is compared with the occurrence of the failure. The weights are adjusted until the output of the ANN corresponds to the occurrence of each past pipeline failure. The initial and final weights for this example are listed in Table 6. The model of this example could be used to predict when and where a future pipeline failure might occur.

Another example in which the method of various embodiments of the present invention could be utilized is predicting the future needs for an electrical power distribution network. In preferred embodiments, the method begins with obtaining an analysis of at least twenty-five power distribution networks. Next, a list of variables associated with power distribution networks is created. Weights are assigned to each variable. One possible set of variables associated with power distribution networks is listed in Table 7. Other variables could be added as experience determines they are relevant to the prediction.

TABLE 7

Listing of variables associated with power distribution networks

| Variables | Initial Weighting For ANN's | Final Weighting For ANN's |
|---|---|---|
| Current are served | 7% | 4% |
| Population of current service area | 7% | 5% |
| Population growth of current service area | 7% | 9% |
| Current usage by household | 7% | 10% |
| Projected future usage by household | 7% | 8% |
| Age of existing service area network | 7% | 6% |
| Industrial growth potential of current service area | 7% | 8% |
| Geographic growth of service area | 7% | 9% |
| Growth demand of new service area | 7% | 10% |
| Cost of enhancing existing service area | 7% | 4% |
| Revenues generated by enhancing existing service area | 7% | 5% |
| Cost of enhancing new area service | 7% | 6% |
| Revenues projected from enhanced new service area | 7% | 10% |
| Projected life of new service area network | 7% | 5% |
| Miscellaneous | 2% | 1% |
|  | 100% | 100% |

An ANN is chosen and trained with the data from existing power distribution networks. For each network, the existing power distribution network data is applied and an output of the ANN is compared with the network data. The weights are adjusted until the output of the ANN corresponds to the existing power distribution network data. The initial and final weights for this example are listed in Table 7.

In various embodiments, this model can be used to predict how large of an area can be served with the current electrical power distribution network. The model can also predict the enhancement of the current network as well as projecting the next power distribution grid.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A method of predicting a future occurrence of an event, the method comprising the steps of:
    obtaining a history of past occurrences of the event;
    creating a plurality of variables associated with the event, including a geographic location of the event;
    assigning a weight to each variable;
    creating an artificial neural network; and
    training the artificial neural network with the history of past occurrences of the event to predict the future occurrence of the event, including the steps—
        applying the variables, including the geographic location of the event, to the artificial neural network for each past occurrence of the event,
        comparing an output of the network with each past occurrence of the event, and
        adjusting the weights of the variables such that the output of the network corresponds to each past occurrence of the event.

2. The method of claim 1, wherein the event is selected from the group consisting of worker's compensation injuries and acute medical situations.

3. The method of claim 1, wherein the variables further include environmental conditions during the event.

4. The method of claim 1, wherein the variables further include ages of entities involved with the event.

5. The method of claim 1, wherein the variables further include sizes of entities involved with the event.

6. The method of claim 1, wherein the variables further include shapes of entities involved with the event.

7. The method of claim 1, wherein the variables further include the physical condition of entities involved with the event.

8. The method of claim 1, wherein the variables further include quantities of entities involved with the event.

9. The method of claim 1, wherein the variables further include costs associated with the event.

10. The method of claim 1, wherein the variables further include measurable properties associated with the event.

11. A method of predicting a future occurrence of an event, the method comprising the steps of:
    obtaining a history of past occurrences of the event;
    creating a plurality of variables associated with the event, the variables including:
        a geographic location of the event,
        environmental conditions during the event,
        ages of entities involved with the event,
        sizes of entities involved with the event,
        shapes of entities involved with the event,
        physical condition of entities involved with the event,
        quantities of entities involved with the event,
        costs associated with the event, and
        measurable properties of entities involved with the event;
    assigning a weight to each variable;
    creating an artificial neural network; and
    training the artificial neural network with the history of past occurrences of the event to predict the future occurrence of the event, including the steps:
        applying the variables, including the geographic location of the event, environmental conditions during the event, ages of entities involved with the event, sizes of entities involved with the event, shapes of entities involved with the event, physical condition of entities involved with the event, quantities of entities involved with the event, costs associated with the event, and measurable properties of entities involved with the event, to the artificial neural network for each past occurrence of the event,
        comparing an output of the network with each past occurrence of the event, and
        adjusting the weights of the variables such that the output of the network corresponds to each past occurrence of the event.

* * * * *